US00PP26800P3

(12) United States Plant Patent
Stewart et al.

(10) Patent No.: US PP26,800 P3
(45) Date of Patent: Jun. 7, 2016

(54) STRAWBERRY PLANT NAMED 'DRISSTRAWFORTYTHREE'

(50) Latin Name: *Fragaria×ananassa*
Varietal Denomination: DrisStrawFortyThree

(71) Applicant: DRISCOLL STRAWBERRY ASSOCIATES, INC., Watsonville, CA (US)

(72) Inventors: Philip J. Stewart, Watsonville, CA (US); Renae Robertson, Santa Maria, CA (US); Joanne F. Coss, Pebble Beach, CA (US); Martin P. Madesko, Aptos, CA (US); Agustin M. Renteria, Royal Oaks, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 90 days.

(21) Appl. No.: 14/121,764

(22) Filed: Oct. 15, 2014

(65) Prior Publication Data

US 2016/0113175 P1 Apr. 21, 2016

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawFortyThree' particularly characterized by dark orange-red colored fruit, early time of flowering and early harvest maturity, is disclosed.

3 Drawing Sheets

Genus and species: *Fragaria×ananassa.*
Variety denomination: 'DrisStrawFortyThree'.

BACKGROUND OF THE NEW PLANT

The present invention relates to a new and distinct strawberry variety designated 'DrisStrawFortyThree' and botanically known as *Fragaria×ananassa.* This new strawberry variety was discovered in Monterey County, Calif. in June 2009 and originated from a cross between the proprietary female parent '131N177' (unpatented) and the proprietary male parent '96P159' (unpatented). A single plant was selected and asexually propagated via tissue culture and vegetative cuttings in Shasta County, Calif.

'DrisStrawFortyThree' underwent further testing in Santa Barbara County, Calif. for five years (2009-2014). The present invention has been found to retain its distinctive characteristics through successive asexual propagations via stolons and tissue culture.

Plant Breeder's Rights for this variety have not been applied for. 'DrisStrawFortyThree' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Santa Barbara County, Calif.

1. Dark orange-red colored fruit;
2. Early time of flowering; and
3. Early harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from nine-month-old plants.

Figure 1:
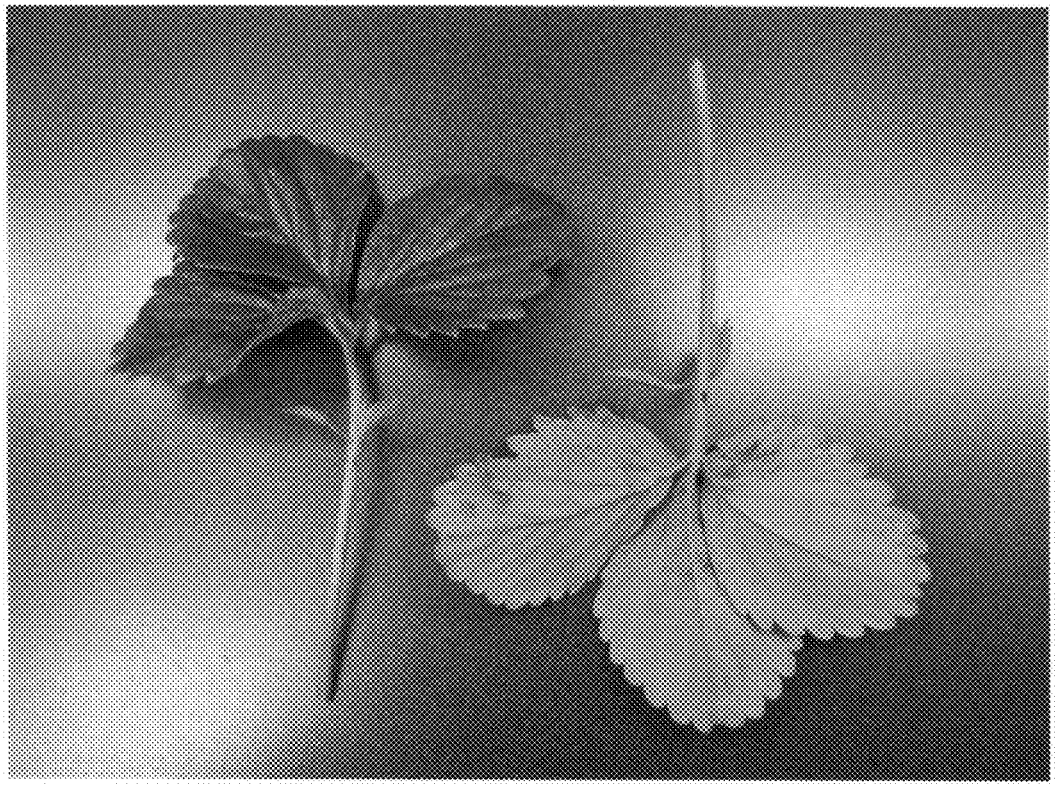
Figure 2:
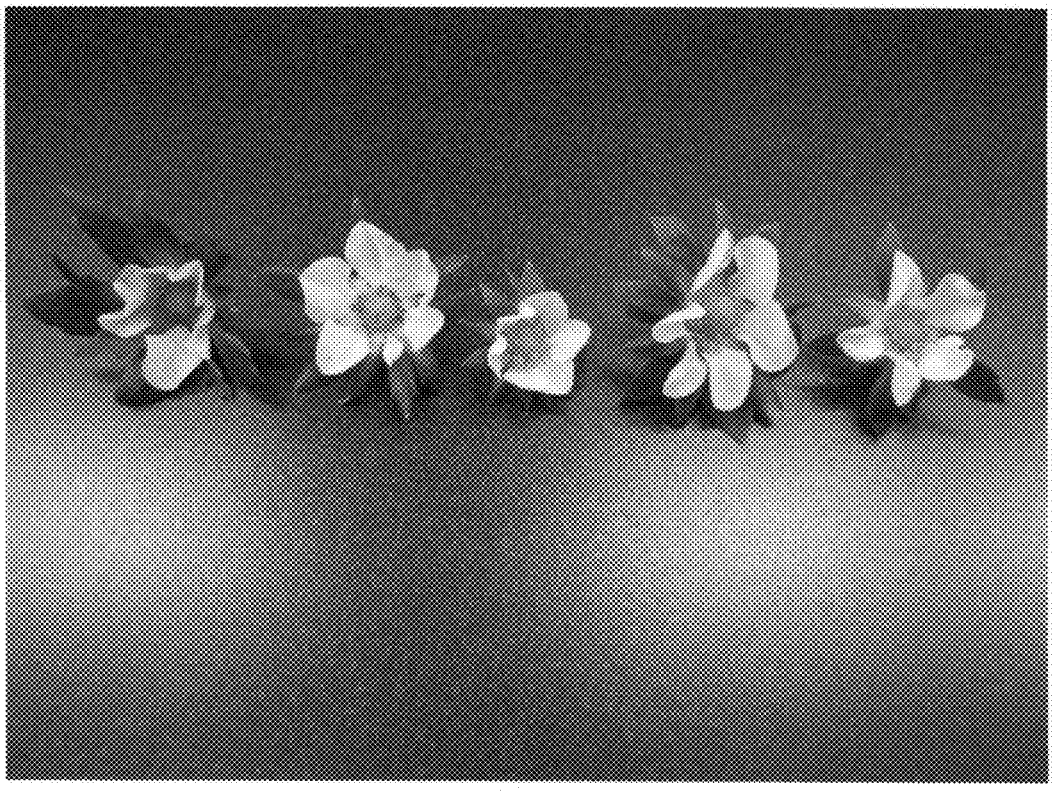
Figure 3:
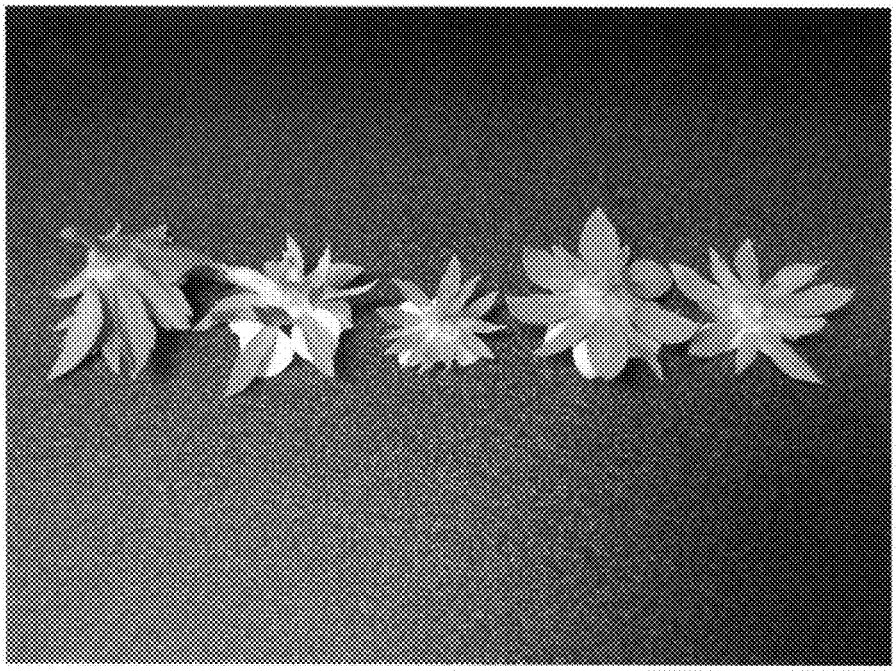
Figure 4:
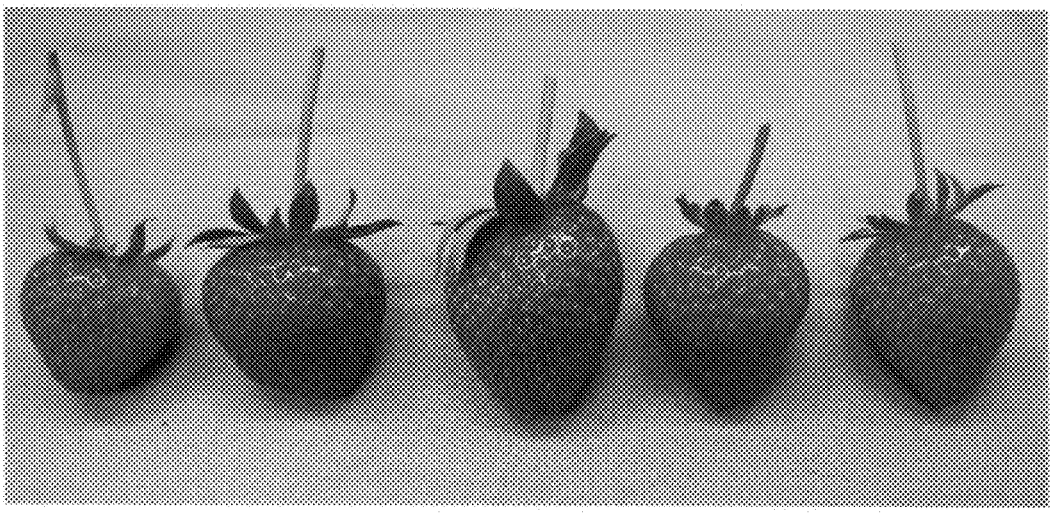
Figure 5:
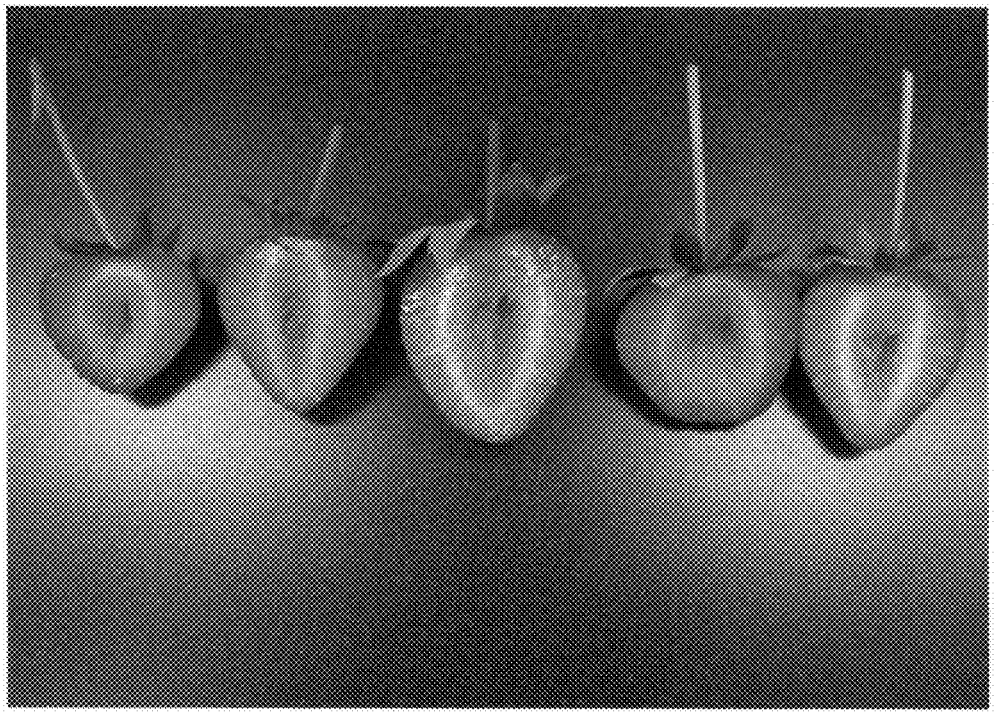
Figure 6:
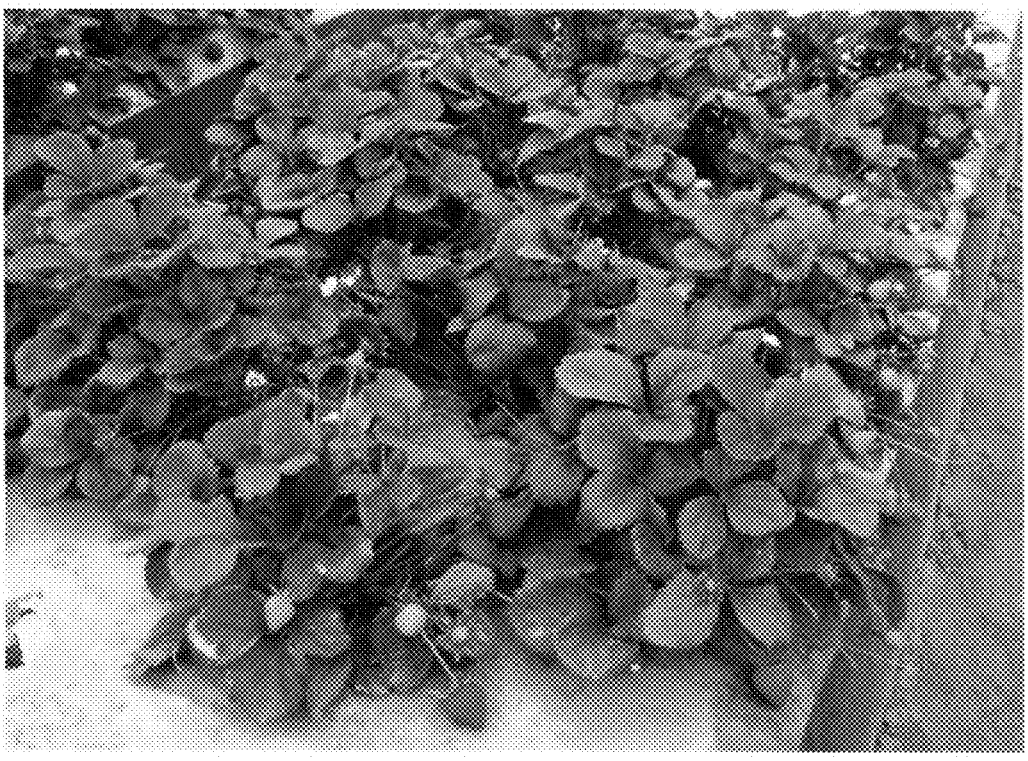

FIG. 1 shows upper and lower surfaces of the leaves of the plant with three leaflets.
FIG. 2 shows the upper surfaces of the flowers.
FIG. 3 shows the lower surfaces of the flowers.
FIG. 4 shows the whole fruit.
FIG. 5 shows the fruit in longitudinal cross-section.
FIG. 6 shows the whole plant.

DESCRIPTION OF THE NEW VARIETY

The following detailed descriptions set forth the distinctive characteristics of 'DrisStrawFortyThree'. The data which define these characteristics is based on observations taken in Santa Barbara County, Calif. from 2009 to 2014. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortyThree' has not been observed under all possible environmental conditions. The botanical description of 'DrisStrawFortyThree' was taken from nine-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawFortyThree'.

Parentage:
- *Female parent.*—The proprietary variety '131N177' (unpatented).
- *Male parent.*—The proprietary variety '96P 159' (unpatented).

Plant:
- *Height.*—28.0 cm.
- *Diameter.*—42.5 cm.
- *Number of crowns/plant.*—4.
- *Habit.*—Flat — spreading.
- *Density of individual plant.*—Medium.
- *Vigor* (*health and hardiness of plant*).—Medium.

Terminal leaflets:
- *Size.*—Medium. Length: 8.8 cm. Width: 7.98 cm. Length/width ratio: 1.1 (As long as broad).
- *Number of teeth/terminal leaflet.*—20.
- *Shape of teeth.*—Rounded to crenate.
- *Color.*—Upper surface: RHS N137A (Medium green). Lower surface: RHS 191A (Medium greyed-green).
- *Shape in cross section.*—Slightly concave.
- *Blistering.*—Medium.
- *Glossiness.*—Medium.
- *Number of leaflets.*—Three only.
- *Shape.*—Orbicular.
- *Base shape.*—Acute.
- *Apex descriptor.*—Complex.
- *Margin.*—Serrate.
- *Margin profile.*—Revolute (margins rolled backwards).
- *Variegation.*—Absent.

Petiole:
- *Length.*—Long; 17.1 cm.
- *Diameter.*—3.90 mm.
- *Pubescence.*—Dense.
- *Pose of hairs.*—Outwards — horizontal.
- *Color.*—RHS 144A (Medium yellow-green).
- *Bract frequency.*—2.

Petiolule:
- *Length.*—10.63 mm.
- *Diameter.*—2.10 mm.
- *Color.*—RHS 144A (Medium yellow-green).

Stipule:
- *Length.*—4.2 cm.
- *Width.*—5.29 mm.
- *Pubescence.*—Medium.
- *Stipule anthocyanin coloration.*—Absent or very weak; RHS 185A (Dark greyed-purple).

Inflorescence:
- *Position relative to foliage.*—Beneath.
- *Number of flowers per plant.*—3.8 (Medium).
- *Time of flowering* (*50% of plants at first flower*).—Early.
- *Flowering interval.*—February-September.
- *Flower size.*—Medium.
- *Flower diameter.*—24.46 mm.
- *Petals.*—Shape: Orbicular. Apex: Rounded. Base: Concavo-convex. Margin: Entire. Spacing: Free. Length: 10.97 mm. Width: 10.69 mm. Length/width ratio: 1.0 (As long as broad). Petal number per flower: 5. Color (upper surface): RHS N155C (White).
- *Calyx.*—Diameter: 41.44 mm. Diameter relative to corolla: Larger. Inner calyx diameter relative to outer: Larger. Insertion of calyx: In a basin — inserted. Pose of calyx segments: Reflexed — upwards. Size of calyx in relation to fruit: Slightly larger. Adherence of calyx: Strong.
- *Sepal.*—Shape: Elliptical. Apex: Truncate. Margin: Entire. Length: 17.59 mm. Width: 8.10 mm. Sepal number: 11.
- *Receptacle color.*—RHS 7A (Medium yellow).
- *Stamen.*—Present. Anther color: RHS 14A (Medium yellow-orange).
- *Pedicel.*—Attitude of hairs: Upwards.

Fruiting truss:
- *Length.*—Medium; 24.3 cm.
- *Diameter at base of truss.*—7.18 mm.
- *Number of berries per fruiting truss.*—4.
- *Attitude at first picking.*—Semi-erect.
- *Color at base of truss.*—RHS 144A (Medium yellow-green).

Fruit:
- *Relative fruit size.*—Medium.
- *Length.*—40.49 mm.
- *Width.*—39.45 mm.
- *Length/width ratio.*—1.0 (As long as broad).
- *Fruit hollow length.*—17.82 mm.
- *Fruit hollow width.*—10.05 mm.
- *Fruit hollow length/width ratio.*—1.8 (Longer than broad).
- *Fruit hollow center* (*cavity*).—Small.
- *Fruit weight.*—20.1 g.
- *Predominant fruit shape.*—Conical.
- *Difference in shape between primary and secondary fruits.*—None or very slight.
- *Evenness of fruit surface.*—Even or very slightly uneven.
- *Fruit skin color.*—RHS N34A (Dark orange-red).
- *Evenness of fruit color.*—Even or very slightly uneven.
- *Fruit glossiness.*—Medium.
- *Achenes.*—Insertion of achenes: Level with surface. Coloration (sunward side of berry): RHS N144A (Light yellow-green). Coloration (shaded side of berry): RHS N144C (Medium yellow-green). Number per berry: 248. Weight (weight of achenes divided by total # seed): 0.1155 g. Width of band without achenes: Narrow.
- *Firmness of flesh* (*when fully ripe*).—Firm.
- *Color of flesh* (*excluding core*).—RHS 42B (Medium red).
- *Color of core.*—RHS 42B (Medium red).
- *Evenness of flesh color.*—Slightly uneven.
- *Distribution of flesh color.*—Marginal and central.
- *Sweetness.*—Medium.
- *Acidity.*—Medium.
- *Texture when tasted.*—Medium.
- *Type of bearing.*—Not everbearing — not remontant.
- *Harvest interval.*—March-September.
- *Harvest maturity.*—Early.
- *Production.*—1223.0 grams per plant.

Disease and pest resistance: Not tested.

Stress resistance:
- *Rain tolerance.*—Moderately resistant.

COMPARISON WITH PARENTAL AND COMMERCIAL VARIETIES

When 'DrisStrawFortyThree' is compared to the female parent '131N177' (unpatented), 'DrisStrawFortyThree' has better flavor and appearance and produces fewer runners in the fruiting field than '131N177'.

When 'DrisStrawFortyThree' is compared to the male parent '96P159' (unpatented), 'DrisStrawFortyThree' has healthier plants and begins fruit production later with fewer culls than '96P159'.

When 'DrisStrawFortyThree' is compared to the commercial variety 'DrisStrawNine' (U.S. Plant Pat. No. 20,733), 'DrisStrawFortyThree' has a flat—spreading growth habit and medium vigor, whereas 'DrisStrawNine' has a upright growth habit and weak vigor. In addition, the insertion of the calyx of 'DrisStrawFortyThree' is in a basin—inserted, whereas 'DrisStrawNine' is level.

When 'DrisStrawFortyThree' is compared to the commercial variety 'San Juan' (U.S. Plant Pat. No. 12,899), 'DrisStrawFortyThree' has a flat—spreading growth habit, whereas 'San Juan' has a globose to flat globose growth habit. Additionally, 'DrisStrawFortyThree' has conical shaped fruit with none or very slight difference in the shape between primary and secondary fruits, whereas 'San Juan' has conical to almost cylindrical shaped fruit with moderate difference in the shape between primary and secondary fruits.

We claim:

1. A new and distinct variety of strawberry plant named 'DrisStrawFortyThree', substantially as illustrated and described herein.

* * * * *